(12) United States Patent
Kakuuchi et al.

(10) Patent No.: US 7,780,292 B2
(45) Date of Patent: Aug. 24, 2010

(54) OPHTHALMOLOGIC EXAMINATION APPARATUS

(75) Inventors: Atsushi Kakuuchi, Hamamatsu (JP);
Kazunori Matsumura, Hamamatsu (JP); Takayoshi Suzuki, Hamamatsu (JP); Yutaka Mizukusa, Chofu (JP); Tadashi Ichihashi, Tokyo (JP)

(73) Assignee: Kowa Company Ltd. (JP)

( * ) Notice: Subject to any disclaimer, the term of this patent is extended or adjusted under 35 U.S.C. 154(b) by 608 days.

(21) Appl. No.: 11/599,261

(22) Filed: Nov. 10, 2006

(65) Prior Publication Data

US 2008/0111970 A1 May 15, 2008

(51) Int. Cl.
*A61B 3/14* (2006.01)
*A61B 3/10* (2006.01)
*A61B 3/02* (2006.01)

(52) U.S. Cl. .................. 351/206; 351/221; 351/243

(58) Field of Classification Search ................ 351/205, 351/206, 211, 214, 216, 221, 222, 240, 243
See application file for complete search history.

(56) References Cited

U.S. PATENT DOCUMENTS 5,508,760 A * 4/1996 Kobayashi et al. .......... 351/221
7,377,642 B2 * 5/2008 Ishihara et al. .............. 351/206

FOREIGN PATENT DOCUMENTS

| JP | 8-117192 | * | 5/1996 |
| JP | 2005323815 | * | 5/2004 |

* cited by examiner

*Primary Examiner*—Joseph Martinez
*Assistant Examiner*—Brandi N Thomas
(74) *Attorney, Agent, or Firm*—Adams & Wilks

(57) ABSTRACT

An ophthalmologic examination apparatus has a main unit housing an illuminating optical system that illuminates a fundus of a subject's eye to be examined and an imaging optical system that images the illuminated eye fundus. First and second attachment units are removably and exchangeably mounted to the main unit for providing different ophthalmologic functions. The first attachment unit houses an imaging device that captures an image of the eye fundus via the imaging optical system housed in the main unit. The second attachment unit houses a light source that emits stimulating light for an electroretinogram and which is projected onto the eye fundus via the imaging optical system housed in the main unit.

17 Claims, 7 Drawing Sheets

OPHTHALMOLOGIC EXAMINATION APPARATUS

BACKGROUND OF THE INVENTION

1. Field of the Invention

The present invention relates to an ophthalmologic examination apparatus having a plurality of ophthalmologic examination functions.

2. Description of the Prior Art

A variety of ophthalmologic examination apparatuses such as fundus cameras and perimeters are conventionally known. A cameras as disclosed in Japanese Patent No. 3359126 is, for example, provided with functions whereby an illuminated eye fundus is once imaged, then magnified and imaged again in the imaging region of a CCD in order to create images of the eye fundus having different magnification ratios. Similarly, a fundus cameras is also known from Japanese Laid-open Patent Application 1979-62691 wherein an illuminated eye fundus can be imaged, the resulting image can be magnified, and the image of the eye fundus can subsequently be divided in a position conjugate with the pupil for stereographical observation.

A fundus camera is also known from Japanese Laid-open Patent Application 1998-155743 wherein a photography unit for photographing an eye fundus is provided separately from a main unit that houses an illuminating optical system and a photographing optical system and an ocular lens are provided on the photography unit side.

However, several problems arise in conventional ophthalmologic examination apparatuses. For example, the apparatuses are primarily intended for a single ophthalmologic examination wherein an eye fundus is observed or imaged, or a visual field is examined. This does not allow various ophthalmologic examinations to be performed. Furthermore, the optical systems of apparatuses that perform a variety of ophthalmologic examinations are complex.

Therefore, an object of the present invention is to provide an ophthalmologic examination apparatus that is capable of performing a variety of ophthalmologic examinations with an inexpensive arrangement.

SUMMARY OF THE INVENTION

An ophthalmologic examination apparatus according to the present invention has a plurality of ophthalmologic examination functions and comprises a main unit for housing an illuminating optical system for illuminating a fundus of an eye to be examined and an imaging optical system for imaging the illuminated fundus of the eye to be examined, and a plurality of attachment units that are removably mounted to the main unit. Each of the attachment units is provided with a different ophthalmologic function to provide a different ophthalmologic function in accordance with the attachment unit mounted to the main unit.

In the present invention, an illuminating optical system for illuminating an eye fundus and an imaging optical system for imaging the illuminated eye fundus, which are both necessary in an ophthalmologic examination, are housed in a main unit. A variety of ophthalmologic examination functions are given to an attachment unit that is mounted to the main unit via a mount. Therefore, a variety of ophthalmologic examinations can be performed merely by selecting the attachment unit and mounting it to the main unit. For example, the attachment unit is provided with a function for planarly or stereographically observing or photographing an imaged eye fundus, a function for emitting stimulating light onto the eye fundus, or a function for spectroscopically analyzing the eye fundus. Merely selecting and mounting it to the fundus camera, an ophthalmologic examination apparatus is provided that is capable of performing an ERG examination or a spectroscopic analysis examination or a visual field examination. Such an ophthalmologic examination apparatus shares most of elements or devices in the main unit and provides a multifunctional, remarkably low-cost examination apparatus.

Further features of the invention, its nature and various advantages will be more apparent from the accompanying drawings and following detailed description of the invention.

DETAILED DESCRIPTION OF THE PREFERRED EMBODIMENTS

Figure 1:
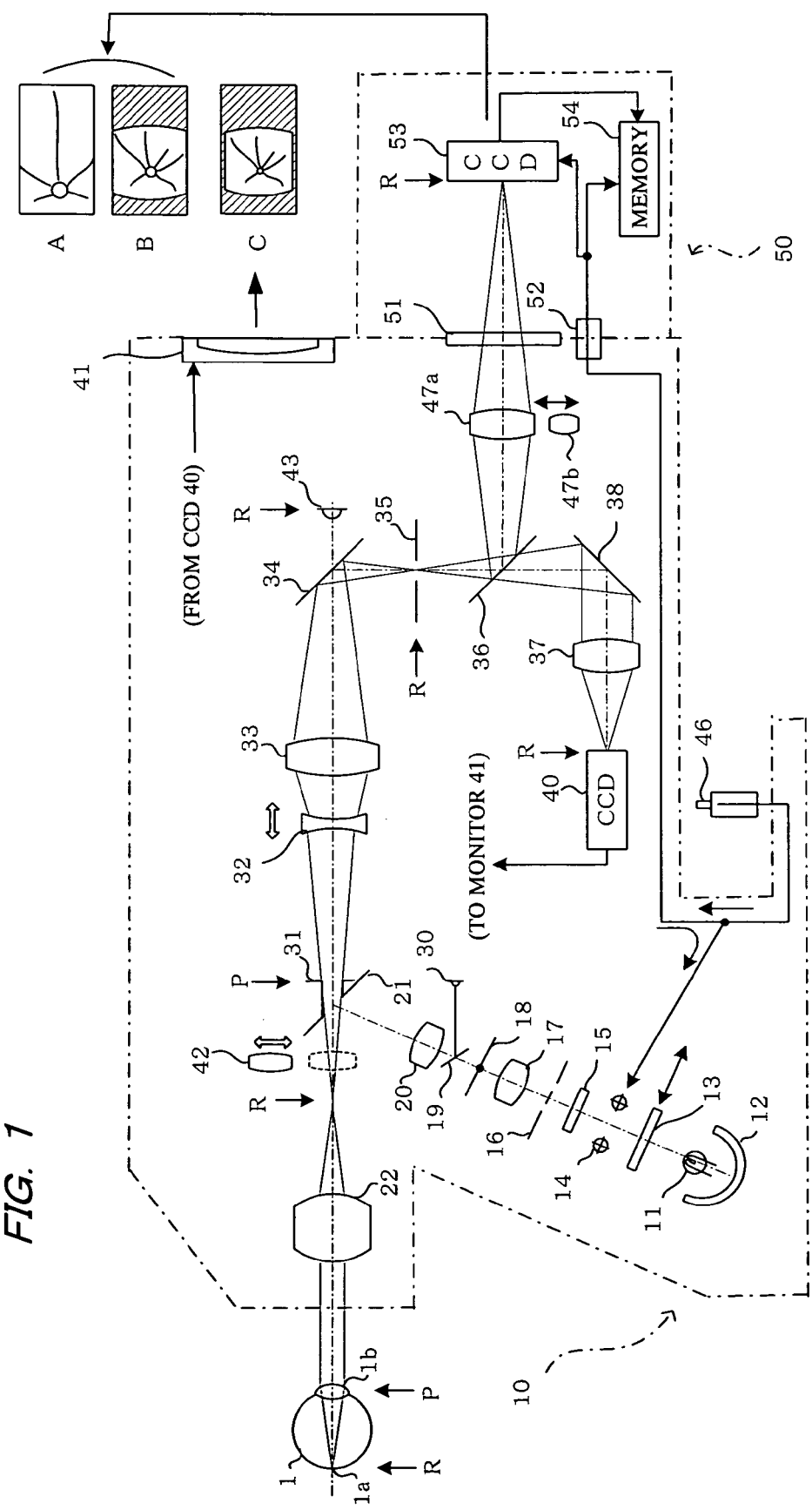
FIG. 1 is an optical diagram showing a first embodiment of an ophthalmologic examination apparatus.

The present invention will now be described in detail with reference to the embodiments shown in the drawings.

The present invention provides an illuminating optical system for illuminating an eye fundus, an imaging optical system for imaging the illuminated eye fundus and other optical systems in a main unit and provides ophthalmologic examination functions or devices to a separate attachment unit. The attachment unit is mounted on the main unit via a mount in order to perform a variety of ophthalmologic examination functions.

FIG. 1 shows a first embodiment of the present invention in which the ophthalmologic examination apparatus is configured as a non-mydriatic fundus camera.

In the ophthalmologic examination apparatus shown in FIG. 1, an illuminating optical system for illuminating an eye fundus and an imaging optical system for imaging the illuminated eye fundus are provided to a main unit 10 of the apparatus. In the illuminating optical system, light emitted from a halogen lamp or another light source 11 together with light reflected by a concave mirror 12 forms into infrared light via a visible-cutting/infrared-transmitting filter 13, passes through a stroboscope 14, diffuses on a diffusion plate 15, and illuminates a ring slit 16 disposed at a position conjugate with an anterior ocular segment (pupil) 1b of an eye 1 to be examined. Illuminating light from the ring slit 16 passes through a lens 17, a black spot plate 18 for eliminating the reflection of an objective lens 22, a half mirror 19 and a relay lens 20; reflects from an apertured total reflection mirror 21 having a central aperture; passes through the objective lens 22; impinges on the eye fundus 1a from the anterior ocular segment 1b of the eye 1 to be examined; and illuminates the eye fundus 1a with infrared light.

Reflected light from the eye fundus 1a arrives via the objective lens 22 and passes through the aperture of the total reflection mirror 21, a photography stop 31, a focus lens 32 and an imaging lens 33, then reflecting from a half mirror 34 and impinging on an infrared-transmitting/visible-reflecting mirror 36 via a field stop 35 disposed in a position conjugate with the eye fundus 1a. Infrared light transmitted through the infrared-transmitting/visible-reflecting mirror 36 reflects from a mirror 38, passes through an imaging lens 37 and impinges on an imaging device 40 composed of an infrared-light-sensitive CCD or the like. A signal from the imaging device 40 is then input to a monitor 41.

Visible light reflected by the mirror 36 enters an attachment unit 50 via either of at least two types of variable-power lenses 47a and 47b and then reaches an imaging device 53 composed of a visible-light-sensitive CCD or the like that is housed in the attachment unit 50. The attachment unit 50 is removably mounted to a mount 51 fixed to the main unit 10 adjacent to a position conjugate with the pupil. When a shutter 46 is manipulated, a shutter-manipulation signal is fed from the shutter 46 via a connector 52 to the imaging device 53 and a memory 54 for storing an image on the imaging device 53. Power is also supplied to the imaging device 53 and memory 54 from the main unit 10 via the connector 52.

In such an imaging optical system, the position conjugate with the fundus 1a of the eye 1 to be examined is indicated by R, and the position conjugate with the anterior ocular segment (particularly the pupil) is indicated by P. The field stop 35 is disposed in a position conjugate with the eye fundus with respect to the optical system (first optical system) composed of the objective lens 22, imaging lens 33, and the like. Therefore, the image of the eye fundus produced by the optical system is formed adjacent to the field stop 35. In addition, the imaging plane of the imaging device 40 is disposed in a position conjugate with the field stop 35 relative to the imaging lens 37, and the imaging plane of the imaging device 53 is disposed in a position conjugate with the field stop 35 relative to the variable-power lenses 47a and 47b (second optical system). The eye fundus image on the field stop 35 is accordingly again created on the imaging devices 40 and 53 by the imaging lens 37 and the variable-power lenses 47a and 47b.

In such a configuration, the visible-cutting/infrared-transmitting filter 13 is inserted into the illuminating optical path. Therefore, the eye fundus is illuminated by infrared light and an image of the eye fundus is produced at the position of the field stop 35 by the objective lens 22, focus lens 32, and imaging lens 33. The eye fundus image of the field stop 35 is transmitted by the infrared-transmitting/visible-reflecting mirror 36 and is again created on the imaging region of the imaging device 40 by the imaging lens 37. Therefore, the image of the eye fundus is displayed as a black-and-white image on a monitor 41. This allows the image of the eye fundus to be observed via the monitor 41 by the examiner.

A focus-dot light source 30 is provided to the illuminating optical system. The light beam from the light source 30 impinges on the eye fundus 1a via the half mirror 19. The position of the focus dot changes in accordance with the movement of the focus lens 32, so that the examiner can observe the focus dot and bring the eye to be examined into focus. An anterior ocular segment lens 42 is inserted into the optical path at the initial stage of alignment. The examiner can accordingly verify the image of the anterior ocular segment 1b of the eye 1 to be examined using the monitor 41. During alignment or focusing, an internal fixation lamp 43 is turned on, and the examiner can reliably perform alignment or focusing by bringing the attention of the person being examined to the fixation lamp.

When the apparatus has been aligned, the shutter switch 46 is operated to produce a shutter operation signal, which is input to the imaging device 53 of the attachment unit 50 and to the memory 54 via the connector 52. This enables the imaging device 53 to be activated to prepare an operation for capturing a still image of the eye fundus. A signal for initiating the emission of light (light regulating signal) is transmitted from the imaging device 53 to the stroboscope 14 in synchronization with the operation signal of the shutter switch 46, thus enabling light to be emitted therefrom. The image of the eye fundus illuminated by light emitted from the stroboscope 14 is created at the position of the field stop 35 and is then recreated on the imaging region of the imaging device 53 by the variable-power lens 47a (47b). The imaging device 53 therefore captures the eye fundus image as a still image.

The still image created by the imaging device 53 is saved in the memory 54 in the attachment unit 50. The still image saved in the memory 54 is loaded into an external computer (not shown), displayed on the monitor 41, or output to a printer (not shown). Alternatively, the memory 54 can itself be made into a cartridge and configured to be detachable from the attachment unit 50. When the cartridge is introduced into another device, the contents of the memory can be read by this other device.

The image of the eye fundus can also be produced with a variable photographic magnification ratio with the aid of the variable-power lenses 47a, 47b disposed on the imaging optical system or with the aid of a zoom lens in place of the variable-power lenses. When the ratio is high, an expanded image of the eye fundus is captured without any image of the field stop 35. When the ratio is low, an image of the eye fundus is captured together with the image of the field stop. For example, images that have been captured by setting the ratio to two values, retrieved from the memory 54 and displayed on the monitor 41 are schematically shown as symbols A and B in the upper right part of FIG. 1. The symbol A indicates an image of the eye fundus captured using a high magnification ratio, while the symbol B shows an image of the eye fundus captured using a low magnification ratio. It can be understood that the image of the field stop is also captured in the photography of low magnification ratio, as is shown by hatching in the periphery of the image B. The examiner can thereby determine an approximate capture ratio by viewing the appearance of the field stop in the image.

On the other hand, the image received by the imaging device 40 disposed on the observation optical system receives no magnification of the variable-power lenses and the examiner can observe the black-and-white image at the same magnification ratio on the monitor 41. To facilitate alignment, the magnification ratio of the optical system leading to the imaging device 40 may be set so that the imaging device can capture an image C having a wider region than the region captured by the imaging device 53. Alignment using the imaging device 40 can thereby always be performed at a wide angle regardless of the magnification of the variable-power lens 47a (47b).

Figure 2:
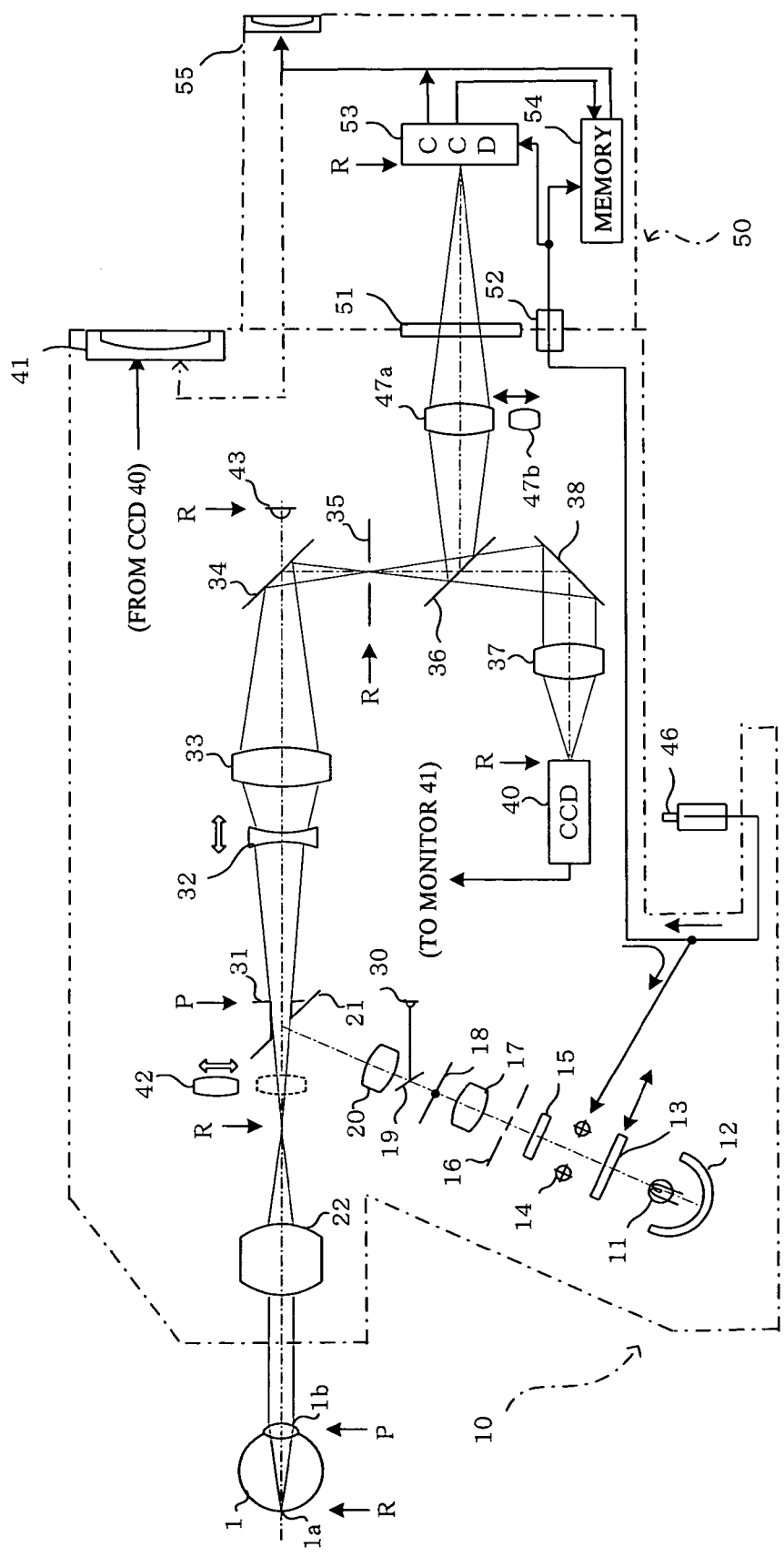
FIG. 2 is an optical diagram showing a second embodiment of an ophthalmologic examination apparatus.

FIG. 2 shows another embodiment. The same numeric symbols are applied to parts having the same or similar functions, and detailed descriptions thereof have accordingly been omitted. The ophthalmologic examination apparatus of this embodiment can be used as a mydriatic/non-mydriatic fundus cameras. The attachment unit 50 is provided with a monitor 55 to which the imaging device 53 and the memory 54 are connected. A signal from the imaging device 53 or a signal from the memory 54 is sent to the monitor 55, and an image of the eye fundus can be displayed thereon.

When the ophthalmologic examination apparatus is used as a non-mydriatic fundus cameras, a visible-cutting/infrared-transmitting filter 13 is inserted into the optical path and the examiner can observe the image of the eye fundus from the imaging device 40 in the same manner as in the first embodiment. Conversely, when used as a mydriatic fundus camera, the visible-cutting/infrared-transmitting filter 13 is retracted from the optical path, and the eye fundus is irradiated with visible light. The examiner therefore photographs the eye fundus using the imaging device 53 and observes the image of the eye fundus displayed on the monitor 55.

The image of the eye fundus captured as a still image by the imaging device 53, under mydriatic or non-mydriatic mode, can be directly displayed on the monitor 55, or can temporarily be stored in the memory 54, retrieved from the memory and then displayed on the monitor 55.

In the second embodiment, the monitor 55 can be used in place of the monitor 41 of the main unit 10. Alternatively, a monitor can be provided to the imaging device 53 or a monitor can be provided to the exterior of the attachment unit 50. When the monitor 41 is used, the signals from the imaging device 53 and the memory 54 are directed to the monitor 41, as indicated by the dashed line.

The visible-cutting/infrared-transmitting filter 13 is inserted into or retracted from the optical path in accordance with mydriatic and non-mydriatic modes. The display of the images from the imaging devices 40 and 53 in both the modes is therefore automatically switched in accordance with the insertion and retract of the filter 13.

In the mydriatic mode, an infrared-cutting/visible-transmitting filter may be inserted into the optical path in place of the filter 13 in order to protect the eye to be examined.

Figure 3:
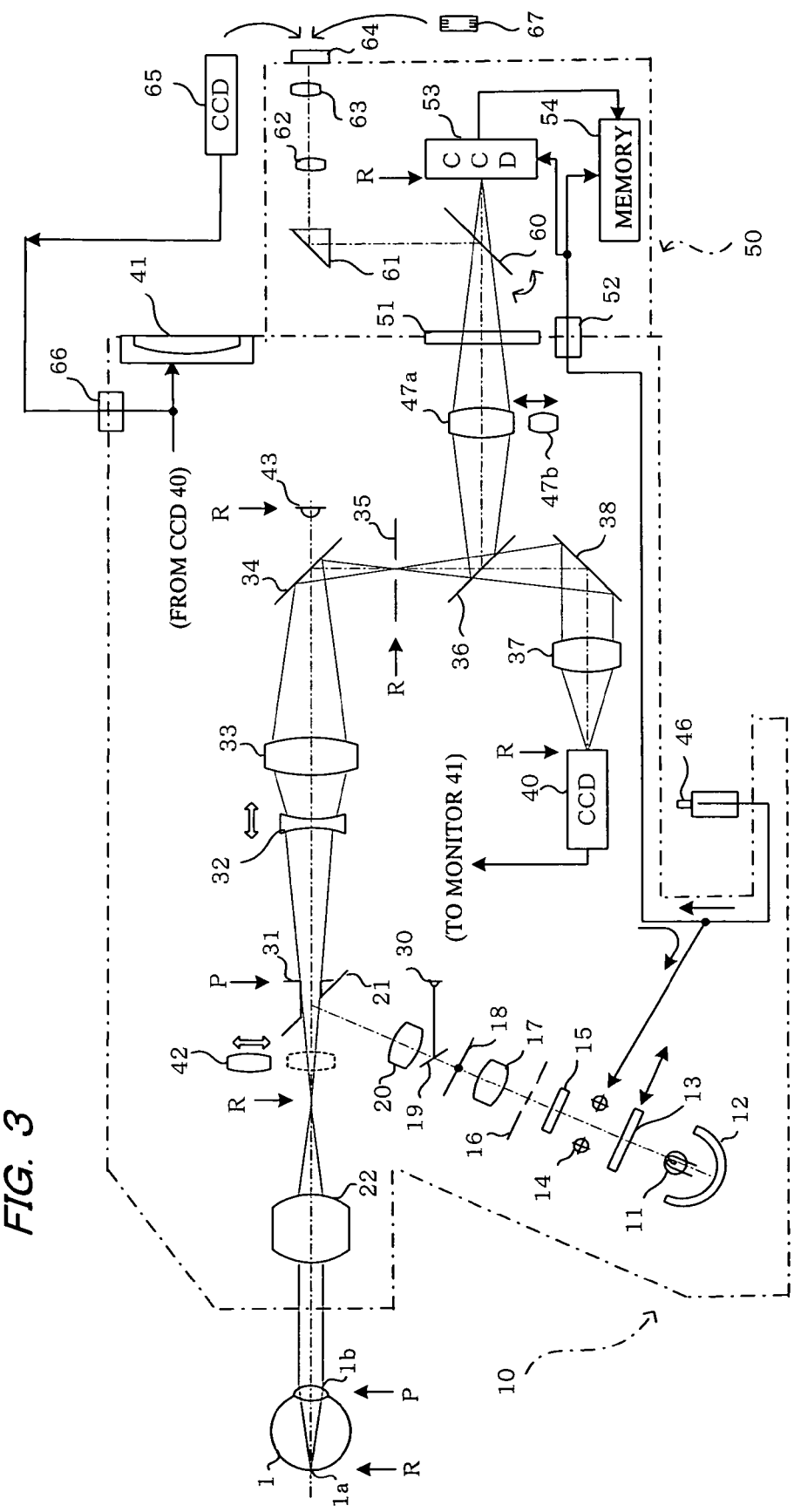
FIG. 3 is an optical diagram showing a third embodiment of an ophthalmologic examination apparatus.
Figure 7:
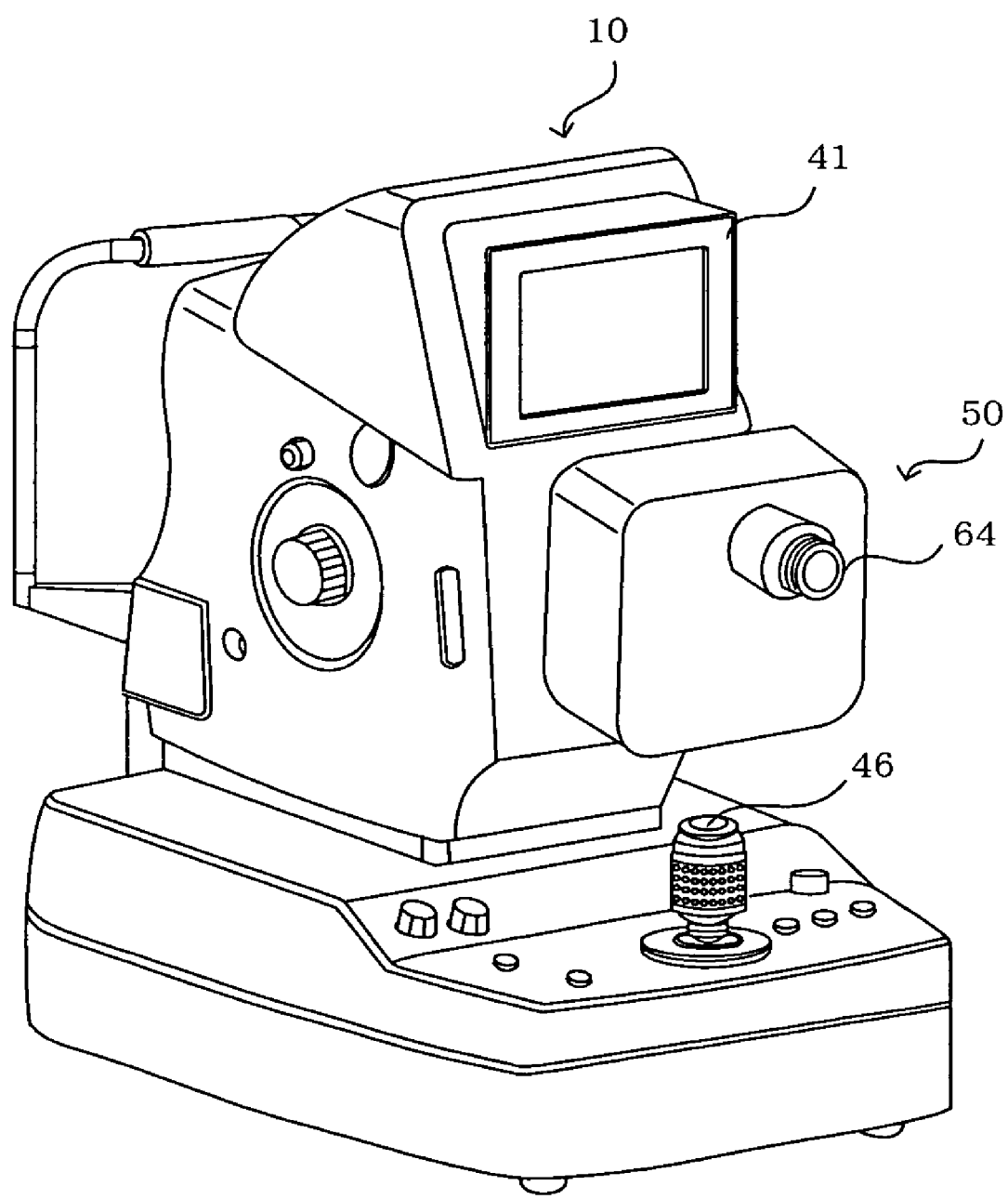
FIG. 7 is a perspective view showing an outer appearance of an ophthalmologic examination apparatus when an attachment unit has been mounted.

FIG. 3 shows a third embodiment in which the ophthalmologic examination apparatus is used as a mydriatic and non-mydriatic fundus cameras in the same manner as in FIG. 2. In FIG. 3, the same numeric symbols are applied to parts having functions that are the same as or similar to those of FIGS. 1 and 2, and detailed descriptions thereof have accordingly been omitted. An appearance of this embodiment is shown in FIG. 7.

In this embodiment, an ocular function is provided to the attachment unit 50, and a return mirror 60 is disposed in the optical path between the mount 51 and the imaging device 53. When the return mirror 60 is in the indicated position, the image of the eye fundus reflected by the return mirror 60 is guided to an ocular lens 63 via a prism 61 and a lens 62, and the image of the eye fundus can be observed via the ocular lens 63. In this instance, a cap (light shielding means) 67 is mounted on a viewing hole 64 of an eyepiece in order to prevent stray light from entering when the device is not in use. The ocular lens 63 is placed near the monitor 55 of the second embodiment and is preferably disposed in a position that corresponds to the optical axis of the objective lens 22 to a degree whereby the monitor 41 in the main unit and the ocular lens will not greatly interfere with one another. The examiner can thereby readily perform alignment.

A separate imaging device 65 composed of a CCD can be mounted to the viewing hole 64. An image of the eye fundus from the imaging device 65 is sent to the monitor 41 via a connecter 66, and can be displayed on the monitor 41. A separate monitor may be used, but a less costly configuration can be achieved if the monitor 41 within the main unit 10 is used.

In such a configuration, when the device is used as a non-mydriatic fundus cameras, a visible-cutting/infrared-transmitting filter 13 is inserted into the optical path during observation in the same manner as in the first and second embodiments, the image of the eye fundus from the imaging device 40 is displayed on the monitor 41, and the examiner performs alignment and focusing while viewing the image of the eye fundus. Conversely, when the device is used as a mydriatic fundus cameras, the visible-cutting/infrared-transmitting filter 13 is withdrawn from the optical path, and the image of the eye fundus irradiated with visible light is reflected by the mirror 36, transmitted by a variable-power lens, reflected by the return mirror 60 and observed via the ocular lens 63. Instead of being observed via the ocular lens 63, the image of the eye fundus can also be observed by mounting a CCD or another imaging device 65 on the viewing hole 64 and displaying the image of the eye fundus from the imaging device 65 on the monitor 41.

During image capture in both the non-mydriatic and mydriatic modes, the return mirror 60 is kept out of the optical path, the image of the eye fundus captured by the imaging device 53 is stored in the memory 54 and the stored image is exported to an external computer, displayed on the monitor 41, or output to a printer. If the memory 54 can be removed, the contents of the memory can be read by another device once the memory has been introduced into the other machine.

Advantages are realized with this embodiment in that direct eye observation via the ocular lens can be performed at the same magnification ratio as the image capture magnification ratio, and in that alignment by the imaging device 40 can always be performed at a wide angle regardless of the magnification used, as is the same with the first embodiment.

Figure 4:
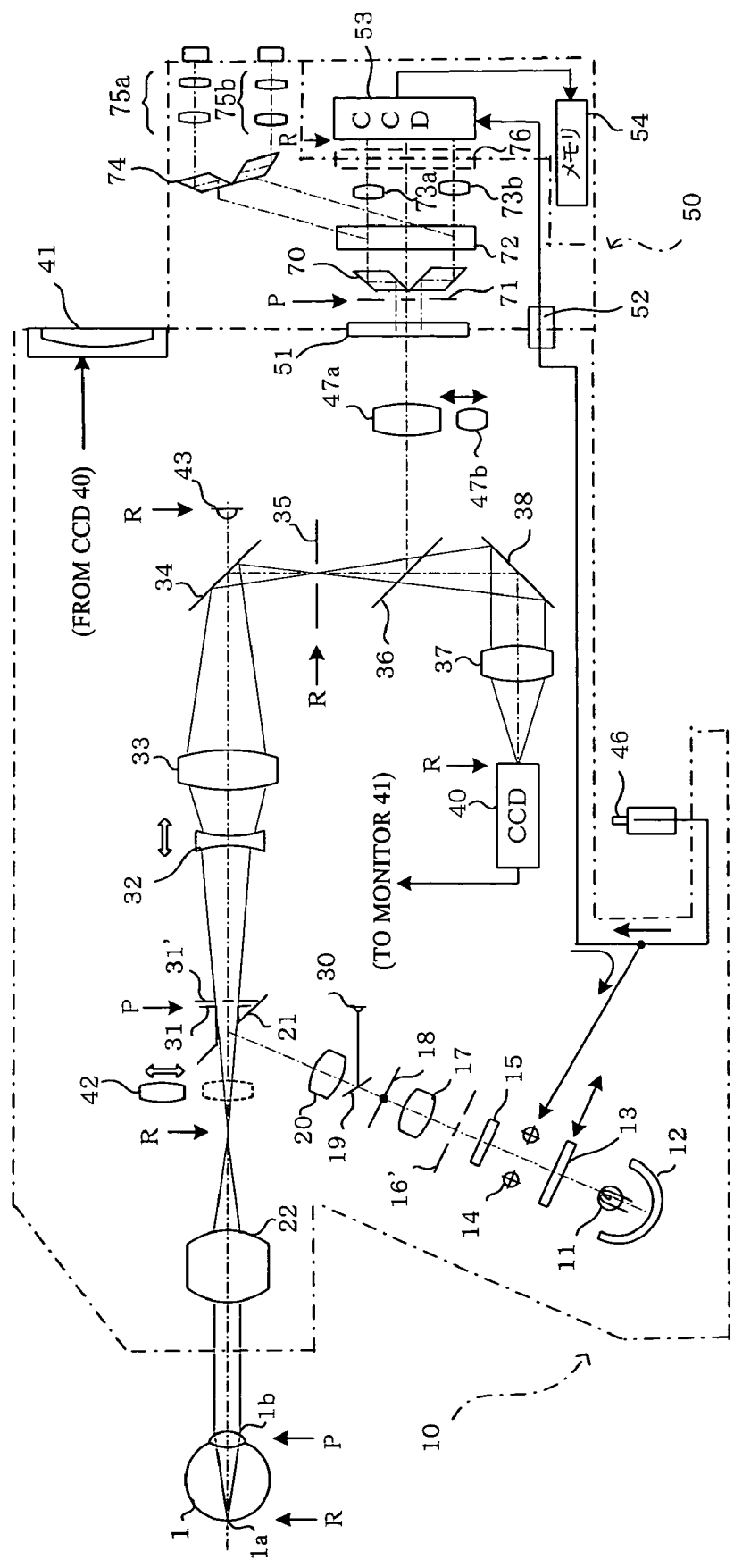
FIG. 4 is an optical diagram showing a fourth embodiment of an ophthalmologic examination apparatus.

FIG. 4 shows a still further embodiment in which the ophthalmologic examination apparatus is used as a mydriatic and non-mydriatic fundus cameras in the same manner as in FIGS. 2 and 3. In FIG. 4, the same numeric symbols are applied to parts having functions that are the same as or similar to those of FIGS. 1, 2 and 3, and detailed descriptions thereof have been omitted.

In the embodiment of FIG. 4, the ophthalmologic examination apparatus has a function whereby an eye fundus can be photographed for stereographical observation. For this purpose, a plurality of apertures 31' for dividing light beams is introduced into the optical path in proximity to the photography stop 31. A dividing prism (optical path dividing means) 70 is additionally provided in the attachment unit 50, and a plurality of aperture stops 71 is disposed directly before the dividing prism 70 in a position P conjugate with the pupil of the anterior ocular segment of the eye to be examined. An image of the eye fundus that has passed through the dividing prism 70 is received by an interpupillary adjustment prism 74 via a return mirror 72, and is stereographically observed by the examiner via a binocular ocular unit composed of a right-eye ocular lens 75a and a left-eye ocular lens 75b. If the return mirror 72 is retracted from the optical path, the image of the eye fundus is captured by the imaging device 53 via lenses 73a and 73b for stereographical eye fundus observation. The imaging device 53 is mounted to the attachment unit 50 via an adapter 76. An imaging device used exclusively for stereographical observation can also be mounted in place of this imaging device. A ring slit 16 disposed in the illuminating optical system in the main unit 10 can be exchanged with a ring slit 16' for stereographical observation. The filter 13 is retracted from the optical path when the eye fundus is observed via a binocular ocular unit. In such a configuration, the eye fundus can be observed in a stereographical rather than planar fashion, and the eye fundus can therefore be scanned from multiple angles.

In FIG. 4, the optical elements in the attachment unit 50 and the plurality of aperture 31' are disposed in a direction orthogonal to the page space, but the representation in the drawing is shown from the direction orthogonal to the page space for the sake of simplicity.

In the embodiment of FIG. 4, the plural aperture 31', dividing prism 70, plurality of aperture stops 71, return mirror 72, and lenses 73a, 73b are disposed so that they are respectively introduced into the optical path in accordance with the selection of the variable-power lenses 47a and 47b, e.g. when variable-power lenses having a high magnification ratio have been selected. This allows a preferable configuration to be obtained because the attachment unit 50 does not need to be switched for stereographical photography.

In the first through fourth embodiments, a position P that is conjugate with the pupil exists adjacent to the mount 51. Therefore, an attachment unit having a normal photography function and an attachment unit having a stereographical photography function can readily be used. In addition, alignment by the monitor 41 during stereographical photography involves using a single screen as with normal photography (rather than using a split screen), and the focusing and working dots for normal photography can be used without modification for stereographical photography. Therefore, the examiner can perform alignment without difficulty.

Figure 5:
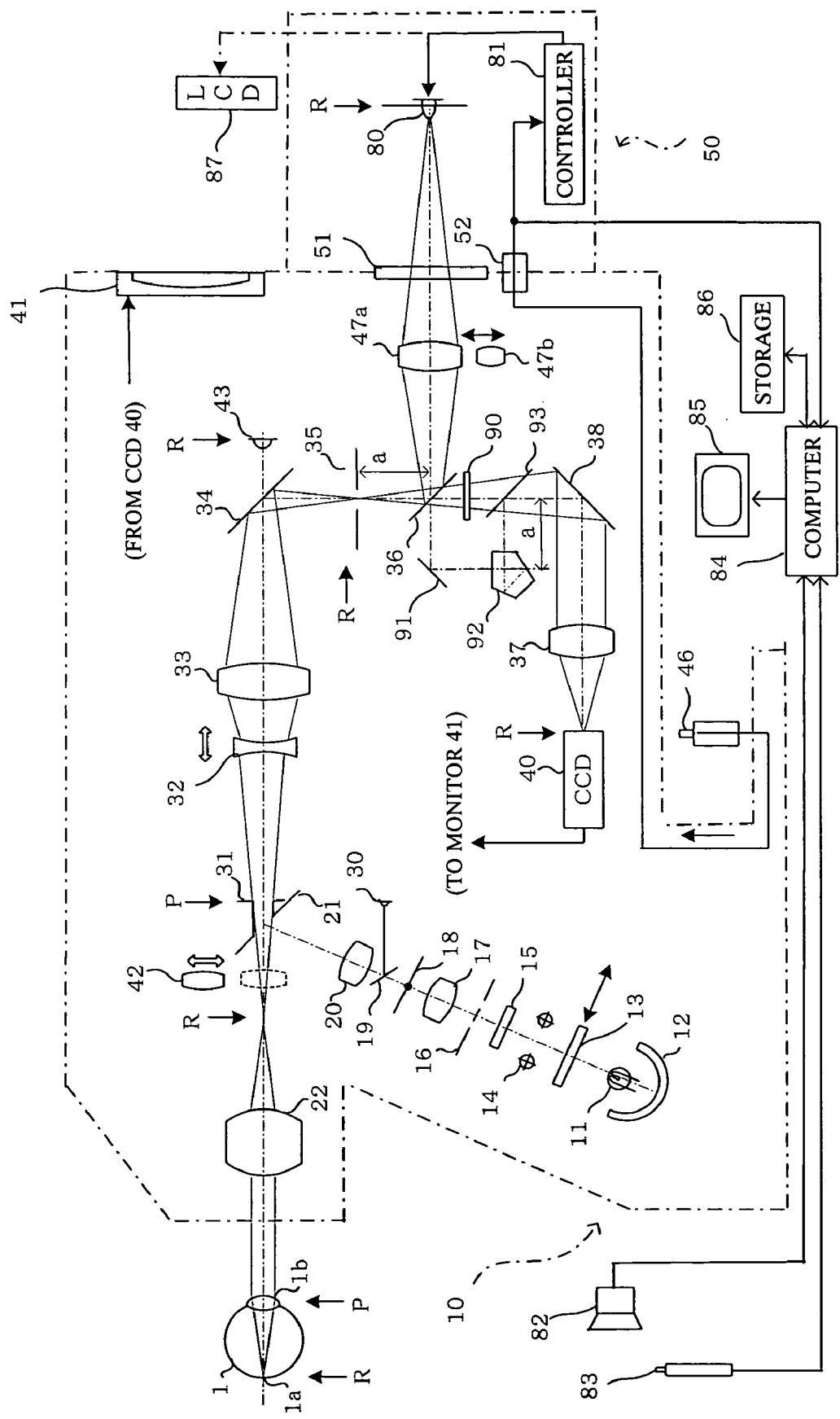
FIG. 5 is an optical diagram showing a fifth embodiment of an ophthalmologic examination apparatus.

FIG. 5 shows a still further embodiment in which the ophthalmologic examination apparatus works as a perimeter. In FIG. 5, the same numeric symbols are applied to parts having functions that are the same as or similar to those of FIGS. 1 through 4, and detailed descriptions thereof have accordingly been omitted.

In the embodiment of FIG. 5, an adjustable light-emitting diode 80 that emits visible light and infrared light and that can be moved manually or automatically in a plane orthogonal to the optical path is provided to the attachment unit 50 in a position R conjugate with the eye fundus in order to allow the apparatus to function as a perimeter. The light-emitting diode 80 functions as a projection target for an ERG (electroretinogram). When the shutter switch 46 is operated, the light-emitting diode 80 is caused by a controller 81 to light up and to emit visible light and infrared light. The visible light is transmitted by the variable-power lens 47a (47b), is reflected by the mirror 36 and is projected as stimulation light on the eye fundus 1a from the pupil 1b of the examined eye via the mirror 34, lenses 33, 32, the aperture of the total reflection mirror 21 and the objective lens 22. An ERG electrode 82 is attached to the eye to be examined A signal from the electrode 82 is input to a computer 84 having a monitor 85 and an external storage device 86. The computer 84 functions as a device for filing the eye fundus image and also produces a retinal potential diagram in accordance with the signals from the electrode 82. The diagram produced is displayed on a monitor 85 and stored in the external storage device 86.

In this embodiment, the target created by the light-emitting diode 80 is transferred to the infrared light-sensitive imaging device 40. Infrared light from the light-emitting diode 80 that has passed through the mirror 36 is reflected by the mirror 38 via a mirror 91, prism 92, and half mirror 93, and is made incident on the imaging device 40 so as to be viewable on the monitor 41. In this instance, the mirror 91 is disposed in a position conjugate with the field stop 35, and the distance a between the field stop 35 and the mirror 36 is equal to the distance between the prism 92 and the mirror 93.

Visible light from the light-emitting diode 80 is reflected by the surface of the imaging lens 33 and returned as reflected light on the imaging device 40. To prevent this, a filter 90 for transmitting infrared light and reflecting visible light is introduced between the infrared-transmitting/visible-reflecting mirror 36 and the half mirror 93. The filter 90 has infrared transmitting characteristics, so that observation light impinges on the imaging device 40 without being cut by the filter 90.

In this embodiment, a liquid crystal display (LCD) device 87 may be disposed in place of the light-emitting diode 80 at a position R of the attachment unit 50 that is conjugate with the eye fundus. The liquid crystal display 87 is connected to the computer 84 via the controller 81. Targets, letters, striped patterns and the like are displayed on the display device 87. The targets and the like displayed are projected onto the fundus of the eye to be examined as stimulation light in the same manner as the target created by the light-emitting diode 80. For example, the target is displayed at a variety of positions on the display device 87 by a computer each time the shutter switch 46 is operated or through a prescribed program. The target displayed is then projected onto the eye fundus and recognized by the person being examined. Upon recognition, the person being examined operates a response switch 83 to transmit a signal to the computer 84, thus enabling the visual field of the person being examined to be measured. In addition, letters can be displayed on the display device 87, and an examination can be performed in regard to whether the person being examined correctly recognizes the letters to examine weak eyesight. In this instance, a computer keyboard, touch panel, or other input means is provided to allow recognized letters to be input.

Alignment must be performed in any ERG examinations that utilize a liquid crystal display device or a light-emitting diode. Alignment is performed by directing infrared light on the eye fundus, capturing the light reflected therefrom using the imaging device 40 and displaying the image of the eye fundus on the monitor 41. In all instances, the shutter switch 46 that is operated after alignment is complete serves as a start switch for starting the examination.

Figure 6:
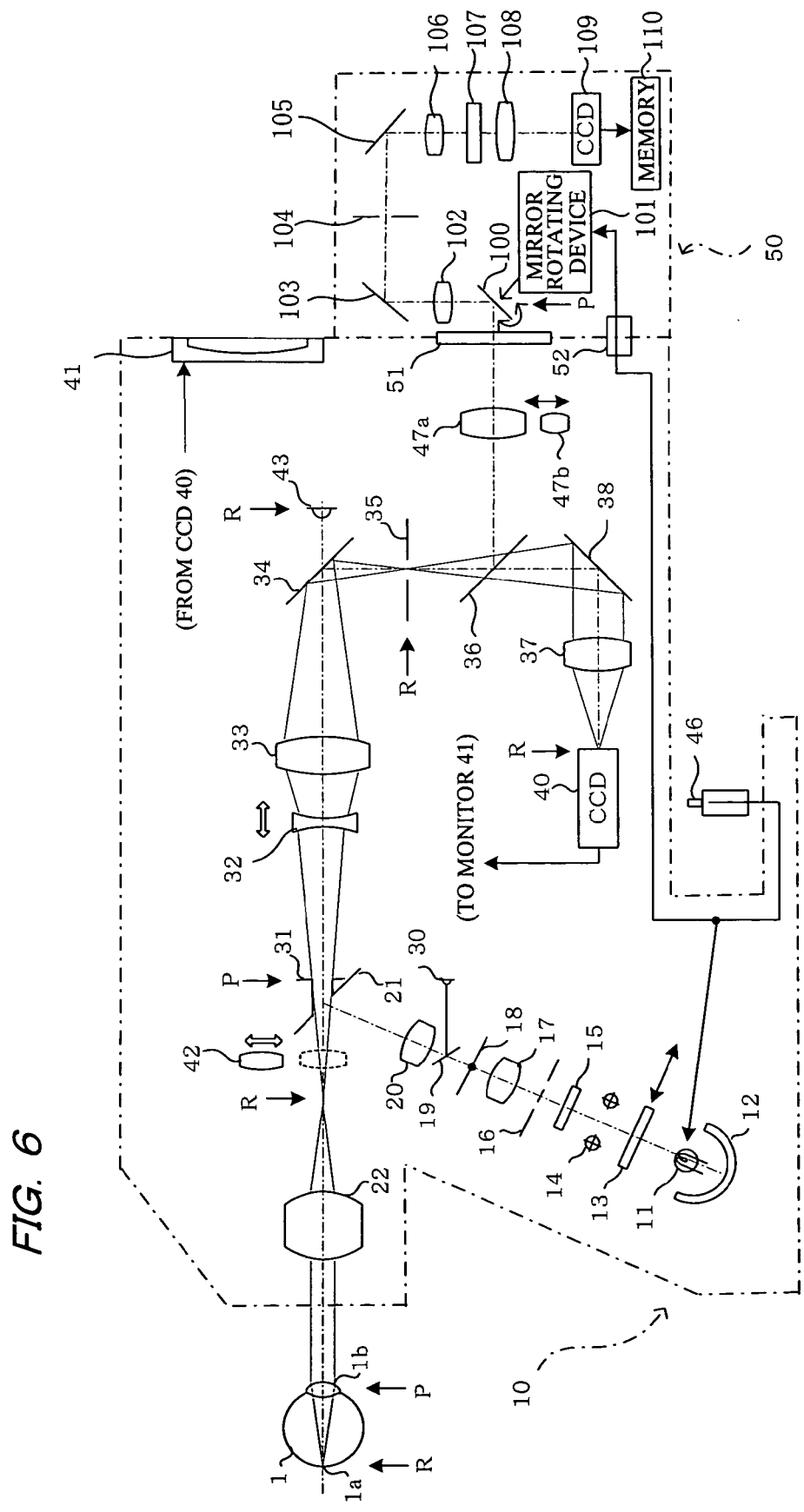
FIG. 6 is an optical diagram showing a sixth embodiment of an ophthalmologic examination apparatus.

FIG. 6 shows a still further embodiment in which the ophthalmologic examination apparatus has a function for spectroscopically analyzing and examining an eye fundus. In FIG. 6, the same numeric symbols are applied to parts having functions that are the same as or similar to those of FIGS. 1 through 5, and detailed descriptions thereof have accordingly been omitted.

In the embodiment of FIG. 6, a mirror 100 that is intermittently driven using a mirror-rotating device 101 composed of a stepping motor or the like is disposed in a position P in the attachment unit 50 conjugate with the pupil in order to spectroscopically analyze an image of the eye fundus. The image of the eye fundus reflected by the mirror 100 is transmitted by a lens 102, reflected by a mirror 103, passed through a slit 104, is reflected by a mirror 105, transmitted by a lens 106, and made incident on a spectral element 107. The spectral element 107 has the same configuration as the prism/grating/prism (PGP) described in Japanese Laid-open Patent Application No. 2002-224041. This element spectroscopically divides the image of the eye fundus slit by the slit 104 over a prescribed wavelength bandwidth in the longitudinal and perpendicular directions of the slit 104. The spectroscopically divided image of the eye fundus passes through a lens 108 and impinges on an imaging device 109 composed of a CCD or the like. A spectral image of the slit image of the eye fundus is thus created and stored in a memory 110.

In such a configuration, when alignment is completed, the shutter switch 46 is operated, the light source 11 is turned on, and the eye fundus is illuminated while the mirror 100 is rotated in prescribed steps by the stepping motor. A line position of the image of the eye fundus created by the slit 104 changes in accordance with the rotation of the mirror, and slit images at the line positions of the eye fundus are captured by the imaging device 109 in accordance with the position of the mirror 100. Spectral data of the slit images of the eye fundus at the line positions as captured by the imaging device 109 are loaded into the memory 110 in synchronization with the line positions of the eye fundus obtained from the mirror-rotating device 101, stored for each line and spectroscopically analyzed by a spectral image analyzing device (not shown)

Accordingly, an apparatus having the eye fundus image capture functions of the first and second embodiments can be converted to an apparatus that shares a large portion of the main unit while having a function for spectroscopically analyzing an image of the eye fundus. Such an apparatus can be obtained merely by installing an attachment unit that has a function for spectroscopically analyzing an image of the eye fundus.

What is claimed is:

1. An ophthalmologic examination apparatus having a plurality of ophthalmologic examination functions, the ophthalmologic examination apparatus comprising:
    a main unit housing an illuminating optical system for illuminating a fundus of a subject's eye to be examined and an imaging optical system for imaging the illuminated eye fundus; and
    first and second attachment units removably and exchangeably mounted to the main unit for providing different ophthalmologic functions, the first attachment unit housing an imaging device for capturing an image of the eye fundus via the imaging optical system housed in the main unit, and the second attachment unit housing a light source for emitting stimulating light for an electroretinogram and which is projected onto the eye fundus via the imaging optical system housed in the main unit.

2. An ophthalmologic examination apparatus according to claim 1; wherein the imaging optical system comprises a first optical system for imaging the eye fundus at a position adjacent to a field stop and a second optical system for re-imaging the image of the eye fundus imaged by the first optical system at a position that lies in the first attachment unit.

3. An ophthalmologic examination apparatus according to claim 1; wherein the first attachment unit is provided with an ocular unit for observing the eye fundus.

4. An ophthalmologic examination apparatus according to claim 3; wherein the ocular unit is provided with light shielding means for preventing stray light from entering into the first attachment unit when the ocular unit is not in use.

5. An ophthalmologic examination apparatus according to claim 3; wherein the ocular unit is provided with a removable imaging device for allowing observation of the eye fundus using a monitor.

6. An ophthalmologic examination apparatus according to claim 1; further comprising a mount for mounting the first and second attachment units to the main unit, the mount lying adjacent to a position that is optically conjugate with a pupil of the eye to be examined.

7. An ophthalmologic examination apparatus according to claim 1; wherein the first attachment unit is provided with optical path dividing means for dividing an optical path of an image of the eye fundus to allow the eye fundus to be photographed for stereographical observation, the optical path dividing means being disposed adjacent to a position conjugate with a pupil of the eye to be examined when the first attachment unit is mounted to the main unit.

8. An ophthalmologic examination apparatus according to claim 7; wherein the optical path dividing means is inserted into the optical path in accordance with a selection of a variable-power lens of the imaging optical system.

9. An ophthalmologic examination apparatus according to claim 1; wherein the main unit has an imaging device for capturing the image of the eye fundus imaged by the imaging optical system.

10. An ophthalmologic examination apparatus according to claim 1; wherein the illuminating optical system illuminates the eye fundus with infrared light or visible light.

11. An ophthalmologic examination apparatus according to claim 9; wherein the imaging device of the main unit is sensitive to infrared light.

12. An ophthalmologic examination apparatus according to claim 9; wherein the imaging device of the main unit photographs a wider area of the eye fundus than does the imaging device of the first attachment unit.

13. An ophthalmologic examination apparatus according to claim 1; wherein the illuminating optical system includes a photography light source for emitting light, an amount of light emitted by the light source being controlled in accordance with activation of the imaging device of the first attachment unit.

14. An ophthalmologic examination apparatus according to claim 13; wherein the main unit has a switch that functions as both a shutter switch that produces a shutter operation signal for the emission of photography light and as a start switch that starts an ophthalmologic examination.

15. An ophthalmologic examination apparatus according to claim 1; wherein the second attachment unit includes display means for displaying a display that is projected onto the eye fundus via the imaging optical system, the display means being exchangeable with the light source housed in the second attachment unit.

16. An ophthalmologic examination apparatus for ophthalmologic examination of a fundus of a subject's eye, the ophthalmologic examination apparatus comprising:
    a main unit having an illuminating optical system that illuminates the eye fundus and an imaging optical system that images the illuminated eye fundus; and
    a plurality of attachment units each for removable and exchangeable attachment to the main unit to provide an ophthalmologic function different from the other of the attachment units, the attachment units comprising a first attachment unit having an imaging device that captures an image of the illuminated eye fundus via the imaging optical system in which light travels from the eye fundus via the image optical system, and a second attachment unit having a light source that emits stimulating light for an electroretinogram so that the light travels to and is projected onto the eye fundus via the imaging optical system.

17. An ophthalmologic examination apparatus according to claim 16; wherein the second attachment unit houses a display device that is exchangeable with the light source and that displays a display that is projected onto the eye fundus via the imaging optical system.

* * * * *